US009980924B2

(12) United States Patent
Meyskens et al.

(10) Patent No.: US 9,980,924 B2
(45) Date of Patent: May 29, 2018

(54) TOPICAL PTEROSTILBENE COMPOSITIONS FOR USE IN TREATING UV-INDUCED LOSS OF BARRIER FUNCTION IN SKIN

(71) Applicant: The Regents of the University of California, Oakland, CA (US)

(72) Inventors: Frank L. Meyskens, Irvine, CA (US); Ryan W. Dellinger, Azusa, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 14/845,173

(22) Filed: Sep. 3, 2015

(65) Prior Publication Data

US 2016/0067194 A1    Mar. 10, 2016

Related U.S. Application Data

(60) Provisional application No. 62/046,068, filed on Sep. 4, 2014.

(51) Int. Cl.
  *A61K 31/09*    (2006.01)
  *A61K 9/00*     (2006.01)
  *A61K 47/26*    (2006.01)
  *A61K 9/08*     (2006.01)

(52) U.S. Cl.
  CPC ............ *A61K 31/09* (2013.01); *A61K 9/0014* (2013.01); *A61K 9/08* (2013.01); *A61K 47/26* (2013.01)

(58) Field of Classification Search
  CPC ...................................................... A61K 31/09
  See application file for complete search history.

(56) References Cited

U.S. PATENT DOCUMENTS

| | | | | |
|---|---|---|---|---|
| 8,841,350 | B2 * | 9/2014 | Bartos | A61K 31/09 514/720 |
| 2002/0183400 | A1 | 12/2002 | Baldo et al. | |
| 2009/0047309 | A1 | 2/2009 | Maes et al. | |
| 2010/0240767 | A1 * | 9/2010 | Majeed | A61K 8/347 514/720 |
| 2012/0289605 | A1 * | 11/2012 | Bartos | A61K 31/09 514/720 |
| 2013/0136778 | A1 * | 5/2013 | Estrela Ariquel | A61K 8/14 424/401 |
| 2013/0296440 | A1 | 11/2013 | Bartos | |
| 2016/0067193 | A1 | 3/2016 | Meyskens, Jr. et al. | |

FOREIGN PATENT DOCUMENTS

| | | |
|---|---|---|
| EP | 2322159 A1 | 5/2011 |
| WO | WO 2011/005406 A2 | 1/2011 |
| WO | WO 2016/036999 A1 | 3/2016 |
| WO | WO 2016/037007 A1 | 3/2016 |

OTHER PUBLICATIONS

U.S. Office Action dated Mar. 10, 2016 issued in U.S. Appl. No. 14/845,171.
PCT International Search Report and Written Opinion dated Dec. 4, 2015 issued in PCT/US2015/048432.
PCT International Search Report and Written Opinion dated Dec. 4, 2015 issued in PCT/US2015/048422.
Allen, et al. (2005) "Ansel's Pharmaceutical Dosage Forms and Drug Delivery Systems, Ninth Edition," *Lippincott, Williams & Wilkins*, i-viii pages (8pages).
Aumont, et al. (2001) "Regioselective and stereospecific glucuronidation of trans-and cis-resveratrol in human," *Arch Biochem Biophys.*, 15;393(2):2819, Abstract—1page.
Chen, et al. (2008) "Glucuronidation of Tobacco-Specific Nitrosamines by UGT2B10," *Drug Metab Dispos.*, 36(5): 824-830, NIH Public Access Author Manuscript—15 pages.
Cichocki, et al. (2008) "Pterostilbene is equally potent as resveratrol in inhibiting 12-O-tetradecanoylphorbol-13-acetate activated NFkappaB, AP-1, COX-2, and iNOS in mouse epidermis," *AMol Nutr Food Res.*, 52 Suppl 1:S62-70, Abstract—1page.
Dellinger, et al. (2006) "Importance of UDP-Glucuronosyltransferase 1a10 (UGT1A10) in the Detoxification of Polycyclic Aromatic Hydrocarbons: Decreased Glucuronidative Activity of the UGT1A10139lys Isoform," *Drug Metab Dispos.*, 34(6): 943-949.
Dellinger, et al. (2007) "Glucuronidation of PhIP and N-OH-PhIP by UDP-glucuronosyltransferase 1A10," *Carcinogenesis*, 28(11): 2412-2418.
Dickinson, et al. (2011) "p38 MAP Kinase Plays a Functional Role in UVB-Induced Mouse Skin Carcinogenesis," *Mol Carcinog.*, 50(6): 469-478, NIH Public Access Author Manuscript—19 pages.
El-Abaseri, et al. (2006) "Ultraviolet irradiation induces keratinocyte proliferation and epidermal hyperplasia through the activation of the epidermal growth factor receptor," *Carcinogenesis*, 27(2):225-231.
Estrela, et al. (2013) "Pterostilbene: Biomedical applications," *Crit Rev Clin Lab Sci.*, 50(3):65-78.
Feddi, et al. (2011) "Abstract 4239: Pterostilbene, a natural polyphenol, elicits full protection against ultraviolet B radiation-induced skin carcinogenesis: Preclinical studies," *Cancer Research—Proceedings: AACR 102nd Annual Meeting 2011 ••* Apr. 2-6, 2011; Orlando, FL, 71;4239, Abstract—1page.
Hougee, et al. (2005) "Selective COX-2 inhibition by a Pterocarpus marsupium extract characterized by pterostilbene, and its activity in healthy human volunteers," *Planta Med.*, 71(5):387-392, Thieme eJournals / Abstract—1page.
Kapetanovic, et al. (2011) "Pharmacokinetics, oral bioavailability, and metabolic profile of resveratrol and its dimethylether analog, pterostilbene, in rats," *Cancer Chemother Pharmacol.*, 68(3): 593-601, NIH Public Access Author Manuscript—19 pages.
Kim, et al. (2011) "Resveratrol Targets Transforming Growth Factor-β2 Signaling to Block UV-Induced Tumor Progression," *Journal of Investigative Dermatology*, 131:195-202.
Maskrey, et al. (2008) "Analysis of eicosanoids and related lipid mediators using mass spectrometry," *Bioanalysis in Oxidative Stress*, 36(5): 1055-1059.
Nickerson (2005) "Sample Preparation of Pharmaceutical Dosage Forms," *Springer*, i-xiv pages (14pages).

(Continued)

*Primary Examiner* — James D. Anderson
(74) *Attorney, Agent, or Firm* — Emily M. Haliday; Weaver Austin Villeneuve & Sampson LLP (57) ABSTRACT

A chemoprotective method for treating, inhibiting or preventing loss of barrier function in skin caused by ultraviolet (UV) light by using an effective amount of pterostilbene is provided. Pharmaceutical and nutraceutical compositions containing pterostilbene suitable for administration to an individual in order to prevent subsequent UV-mediated loss of barrier function in skin are provided.

13 Claims, 3 Drawing Sheets
(2 of 3 Drawing Sheet(s) Filed in Color)

(56) References Cited

OTHER PUBLICATIONS

Nishiwaki, et al. (2004) "Trichothiodystrophy Fibroblasts Are Deficient in the Repair of Ultraviolet-Induced Cyclobutane Pyrimidine Dimers and (6-4)Photoproducts," *J Invest Dermatol*, 122:526-532.

Oba, et al. (2013) "Collagen hydrolysate intake improves the loss of epidermal barrier function and skin elasticity induced by UVB irradiation in hairless mice.," *Photodermatol Photoimmunol Photomed.*, 29(4):204-11, Abstract—2pages.

Papazoglou, et al. (2010) "Noninvasive assessment of Uv-induced skin damage: comparison of optical measurements to histology and MMP expression.," *Photodermatol Photoimmunol Photomed.*, 86(1):138-45, Abstract—1page.

Reagan-Shaw, et al. (2004) "Modulations of critical cell cycle regulatory events during chemoprevention of ultraviolet B-mediated responses by resveratrol in SKH-1 hairless mouse skin," *Oncogene*, 23: 5151-5160.

Riche, Daniel (2010) "Effect of Pterostilbene on Cholesterol, Blood Pressure and Oxidative Stress", *ClinicalTrials.gov*, 4 pages. [retrieved on Jun. 23, 2011] Retrieved from the Internet: URL:http://clinicaltrials.gov/ct2/show/NCT01267227?term=Daniel+Riche&rank=3.

Riche, et al. (2013) "Analysis of Safety from a Human Clinical Trial with Pterostilbene," *Journal of Toxicology*, vol. 2013, Article ID 463595, 5 pages.

Rimando, et al. (2002) "Cancer chemopreventive and antioxidant activities of pterostilbene, a naturally occurring analogue of resveratrol," *J Agric Food Chem.*, 50(12):3453-3457.

Sirerol, et al. (2015) "Topical treatment with pterostilbene, a natural phytoalexin, effectively protects hairless mice against UVB radiation-induced skin damage and carcinogenesis," *Free Radic Biol Med.*, 85:1-11.

* cited by examiner

TOPICAL PTEROSTILBENE COMPOSITIONS FOR USE IN TREATING UV-INDUCED LOSS OF BARRIER FUNCTION IN SKIN

CROSS-REFERENCE TO RELATED APPLICATIONS

This application claims the benefit of U.S. Provisional application No. 62/046,068, filed on Sep. 4, 2014, which is hereby incorporated by reference herein.

STATEMENT REGARDING FEDERALLY SPONSORED RESEARCH

This invention was made with government support under Grant No. P30CA62330, awarded by the National Cancer Institute, and Grant No. R03ES019668, awarded by the National Institute of Environmental Health Sciences. The Government has certain rights in the invention.

FIELD OF THE INVENTION

A chemoprotective method for treating, inhibiting or preventing loss of barrier function in skin caused by ultraviolet (UV) light by using an effective amount of pterostilbene is described. Pharmaceutical and nutraceutical compositions containing pterostilbene suitable for administration to an individual in order to prevent subsequent UV-mediated loss of barrier function in skin are described. Compositions containing pterostilbene may be used in the care or treatment of skin and skin conditions.

BACKGROUND

Skin is the human body's first and best defense against environmental exposures including solar ultraviolet (UV) radiation. Exposure to UV light is a key factor in the development of skin disorders including cancer. Skin cancer is the most prevalent type of cancer in the United States, affecting an estimated one out of every seven Americans (Ndiaye, et al., *Arch. Biochem. Biophys.* (2011) 508: 164-70).

Nonmelanoma skin cancer (NMSC) has increased rapidly in the past two decades and more than one million new cases of non-melanoma skin cancer (NMSC) are diagnosed annually in the United States. It is suspected that this estimate is low as squamous cell carcinoma (SCC) and basal cell carcinoma (BCC) of the skin are not required to be reported and the number of actual cases annually is projected to be over 3 million new cases annually (Wheless, et al., "Nonmelanoma skin cancer and the risk of second primary cancers: a systematic review," *Cancer Epidemiol. Biomarkers Prev.* (2010) 19: 1686-95). Based on IC9 Codes, it is estimated that 5% of the Medicare budget is used in the care of these patients (Rogers, et al., "Incidence estimate of nonmelanoma skin cancer in the United States, 2006," *Arch. Dermatol.* (2010) 146: 283-7).

An estimated 2,700 deaths this year will be the result of NMSC in the US. The majority of these deaths are caused by SCC. Most NMSC, including SCC are caused by sun exposure (including UV-B light) with resultant photocarcinogenesis. Epidemiological data also shows an increased risk of other lethal cancer types in individuals with a history of skin cancer. Thus, it is vital to understand the harmful effects that UV light has on the skin so that effective methods of treatment or prevention can be developed.

Actinic keratoses (AKs) are precancerous cutaneous neoplasms, which can give rise to SCC. They arise as a result of long-term sun exposure. Other causes of AKs and NMSC are UV light from tanning booths or arc welding, x-irradiation, or exposure to certain chemicals. AKs are extremely common lesions and are present in more than 10 million Americans. In one sample population, the yearly rate of progression of an AK to a SCC in an average-risk person in Australia is between 8 and 24 per 10,000. High-risk individuals (those with multiple AKs) have progression rates as high as 12-30 percent over 3 years. Two percent of SCCs originating in AKs may metastasize, and 7 percent recur locally.

Actinic keratoses are treated most commonly with liquid nitrogen or a topical chemotherapeutic agent, such as, for example, 5-fluorouracil. Less commonly they are treated with other topical agents (diclofenac and imiquimod), photodynamic therapy, chemical peels or ablative laser resurfacing. Treatment for NMSC is usually surgical, often resulting in scarring and other morbidities.

In the instant specification, it will be understood that "actinic keratosis" is the proliferative disorder that produces AKs.

While some treatments are known, it would be desirable to proactively prevent or inhibit formation of actinic keratosis, hyperplasia, and/or skin cancers in order to reduce treatment costs, morbidity, and mortality. A lifetime of sun protection is an excellent method for minimizing risk of development of actinic keratosi, hyperplasia, and/or NMSC. However, a large percentage of patients already have extensive photodamage and changing sun-protective behaviors has proven to be difficult.

An ideal chemopreventive agent could achieve regression of precancerous changes, prevent development of NMSC and minimize ultraviolet light associated damage with minimal or no side effects. As noted above, there are topical agents that can remove actinic keratoses but they generally result in significant inflammation at the treatment site. A novel approach is required.

UV-mediated DNA Damage

Ultraviolet (UV) light plays an integral role in the development of numerous skin ailments ranging from aging to cancer. Considerable evidence spanning decades has conclusively demonstrated that UV radiation triggers multiple independent cellular responses. UV radiation is known to penetrate skin where it is absorbed by proteins, lipids and DNA, causing a series of events that result in progressive deterioration of the cellular structure and function of cells (Valacchi, et al., "Cutaneous responses to environmental stressors," *Ann. N. Y. Acad. Sci.* (2012) 1271: 75-81). DNA is the building block of life and its stability is of the utmost importance for the proper functioning of all living cells. UV radiation is one of the most powerful (and common) environmental factors that can cause a wide range of cellular disorders by inducing mutagenic and cytotoxic DNA lesions; most notably cyclobutane-pyrimidine dimers (CPDs) and 6-4 photoproducts (64 pps) (Narayanan, et al., "Ultraviolet radiation and skin cancer," *Int. J. Dermatol.* (2010) 49: 978-86). It is important to note that UV-mediated DNA damage is an early event in a plethora of proliferative cellular disorders. The two major types of UV-induced DNA damage are CPDs and 64 pp (along with their Dewer isomers) (Sinha, R. P. and Hader, D. P., "UV-induced DNA damage and repair: a review," *Photochem. Photobiol. Sci.* (2002) 1: 225-36; and Rastogi, et al., "Molecular mechanisms of ultraviolet radiation-induced DNA damage and repair," *J. Nucleic Acids* (2010) 2010: 592980). These abundant DNA lesions, if unrepaired, can interfere with DNA replication and subsequently cause mutations in DNA. Thus, these lesions can be mutagenic (potentially leading to proliferative disorders) and/or can be cytotoxic (resulting in cell death). 64 pp occur at about one third the frequency of CPDs, but are more mutagenic (Sinha & Hader, 2002). In one embodiment, prevention of these UV-mediated DNA adducts is paramount to guarding against the onset of several proliferative disorders, ranging from aging to cancer.

UV-mediated Hyperplasia

Increased keratinocyte proliferation, resulting in hyperplasia, is another major detrimental effect caused by UV exposure. This thickening of the skin is a direct result of the body trying to protect itself after excessive exposure to UV light. However, epidermal hyperplasia also increases the risk of skin cancer (Bowden, G. T., "Prevention of non-melanoma skin cancer by targeting ultraviolet-B-light signaling," Nat. Rev. Cancer (2004) 4: 23-35). In another embodiment, prevention of UV-mediated hyperplasia is paramount to guarding against the onset of several proliferative disorders, ranging from aging to cancer.

UV-mediated Loss of Barrier Function

Maintaining a water-impermeable barrier between the organism and the environment is an essential function of skin. This barrier function serves to prevent dehydration; which can lead to death of the organism (Jiang, S. J., et al., "Ultraviolet B-induced alterations of the skin barrier and epidermal calcium gradient," Exp. Dermatol. (2007) 16: 985-992). UV light has been demonstrated to disrupt epidermal skin barrier function in a dose-dependent manner (Haratake, A., et al., "UVB-induced alterations in permeability barrier function: roles for epidermal hyperproliferation and thymocyte-mediated response" J. Invest. Dermatol. (1997) 108: 769-775; and prey. citation). Skin barrier dysfunction can be directly assessed by measuring Transepidermal Water Loss (TEWL), which is a measure of skin hydration (Oba, C., et al., "Collagen hydrolysate intake improves the loss of epidermal barrier function and skin elasticity induced by UVB irradiation in hairless mice," Photodermatol. Photoimmunol. Photomed. (2013) 29: 204-11; and prey. citations).

Resveratrol, a natural polyphenol present in grapes and red wine, exerts several beneficial effects including antioxidant, chemopreventative and cardioprotective (Park, K. and Lee, J- H., "Protective effects of resveratrol on UVB-irradiated HaCaT cells through attenuation of the caspase pathway," Oncol. Rep. (2008) 19: 413-7). Several studies have shown that resveratrol prevents UV-B mediated cell damage (including hyperplasia) in mouse skin when given orally or applied topically (Afaq, F., et al., "Prevention of short-term ultraviolet B radiation-mediated damages by resveratrol in SKH-1 hairless mice," Toxicol. Appl. Pharmacol. (2003) 186(1): 28-37; Reagan-Shaw, S., et al., "Modulations of critical cell cycle regulatory events during chemoprevention of ultraviolet B-mediated responses by resveratrol in SKH-1 hairless mouse skin," Oncogene (2004) 23(30): 5151-60; Aziz, M. H., et al., "Prevention of ultraviolet-B radiation damage by resveratrol in mouse skin is mediated via modulation in survivin," Photochem. Photobiol. (2005) 81(1): 25-31; and Kim, K. H., et al. "Resveratrol Targets Transforming Growth Factor-beta2 Signaling to Block UV-Induced Tumor Progression," J. Invest. Dermatol. (2011) 131: 195-202). Resveratrol has been shown to block UV-induced skin cancer progression in several mouse studies (Athar, M., et al., "Resveratrol: a review of preclinical studies for human cancer prevention," Toxicol. Appl. Pharmacol. (2007) 224: 274-83). However, its use in humans as a chemopreventative agent seems to be unlikely (at least as a single agent) due to poor bioavailability (Roupe, K. A., et al. "Pharmacometrics of stilbenes: seguing towards the clinic," Curr. Clin. Pharmacol. (2006) 1: 81-101). Resveratrol is well tolerated in humans, but is readily metabolized (by the UGTs) leading to a short half-life which hinders its effectiveness as a chemopreventative agent (Cottart C. H., et al., "Resveratrol bioavailability and toxicity in humans," Mol. Nutr. Food Res. (2010) 54: 7-16).

SUMMARY

A skin care composition includes pterostilbene for treating, inhibiting or preventing UV-mediated loss of barrier function in human skin.

A method of treating, inhibiting or preventing UV-mediated loss of barrier function in human skin is provided, comprising administering to the individual in need of such treatment an effective amount of the compound pterostilbene (e.g., by topical administration).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

A chemoprotective method for treating, inhibiting or preventing loss of barrier function in skin caused by ultraviolet (UV) light by using an effective amount of pterostilbene has been discovered. Pharmaceutical and nutraceutical compositions containing pterostilbene suitable for administration to an individual in order to prevent subsequent UV-mediated loss of barrier function in skin are described.

The term "effective amount" is used herein to refer to an amount of a pterostilbene that is sufficient to treat, inhibit or prevent UV-mediated loss of barrier function to any degree, e.g., as measured by any means described herein or known in the art (e.g, transepidermal water loss [TEWL], as described herein). An effective amount for treatment (i.e., a therapeutically effective amount) is amount that typically produces any improvement in a condition, such as barrier function, relative to that condition before initiating treatment. "Inhibition" or "prevention" can be determined relative to the results observed in a control individual that is not treated with pterostilbene. The control individual is one that is matched to a treated individual as is standard in the art (e.g., as illustrated in the Examples described below). In various embodiments, an effective amount is an amount sufficient to treat, inhibit or prevent TEWL, UV- mediated DNA damage and/or hyperplasia by at least: 10%, 20%, 30%, 40%, 50%, 60%, 70%, 80%, 90%, or 100%, as compared to a control. An effective amount is typically determined before the chemoprotective methods described herein are carried out.

In some embodiments, "an individual in need of treatment for, inhibition of, or prevention of, loss of barrier function in skin" excludes individuals who have been treated with pterostilbene for a different purpose.

Pterostilbene (3,5-dimethoxy-4'-hydroxy-trans-stilbene) is an orally bioavailable compound with a half life $t_{1/2}$ of about 105 minutes in blood. In contrast, resveratrol has poor bioavailability, and is readily metabolized by UGTs leading to a much shorter half life ($t_{1/2}$ about 14 minutes in blood), which hinders its effectiveness as a chemopreventive agent.

Pterostilbene is a natural product found in grapes and berries. Chemically it is a naturally occurring dimethylated analog of resveratrol, but has a longer half-life (FIG. 1) most likely due to the methyl groups dramatically reducing its metabolism by UGTs (Hougee, S., et al., "Selective COX-2 inhibition by a *Pterocarpus marsupium* extract characterized by pterostilbene, and its activity in healthy human volunteers," *Planta Med*. (2005) 71: 387-92). 2005) 71(5): 387-92). Pterostilbene has been shown to be equally or significantly more potent than resveratrol in several biological assays in mice including inhibition of NF-KB, AP-1 and iNOS activation in mouse skin. Importantly, pterostilbene has been shown to prevent COX-2 activation and 12-O-tetradecanoylphorbol-13-acetate (TPA)-induced tumor formation in mouse epidermis in vivo (Cichocki, M., et al., "Pterostilbene is equally potent as resveratrol in inhibiting 12-O-tetradecanoylphorbol-13-acetate activated NFkappaB, AP-1, COX-2, and iNOS in mouse epidermis," Mol. Nutr. Food Res. (2008) 52 Suppl 1: S62-70).

Herein is described a process using pterostilbene to inhibit, treat or prevent UV mediated loss of barrier function in skin, or other DNA damages in skin associated with UV exposure. Loss of barrier function increases an individual risk for dehydration as well as exposure to environmental stress including carcinogens. Less water loss (as measured by TEWL) indicates less dehydration of skin tissue.

Figure 2:
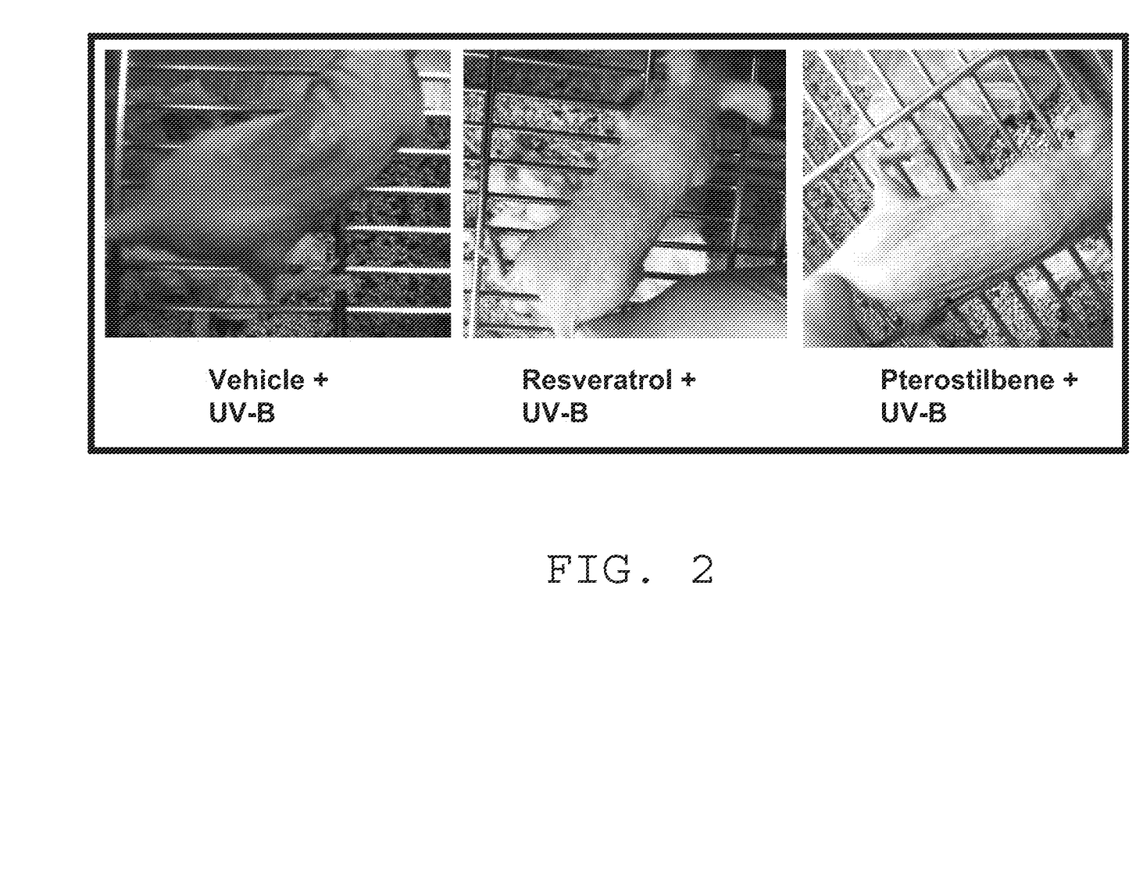
FIG. 2 depicts the manner in which pterostilbene prevents UV-B induced damage in the skin of SKH-1 mice. Mice were treated topically with vehicle alone ('+' acetone), resveratrol or pterostilbene 30 minutes prior to exposure to 180 mJ/cm$^2$ of UV-B. Treatment was repeated every other day for 14 days. Photographs show representative mice after 4th treatment.
Figure 3:
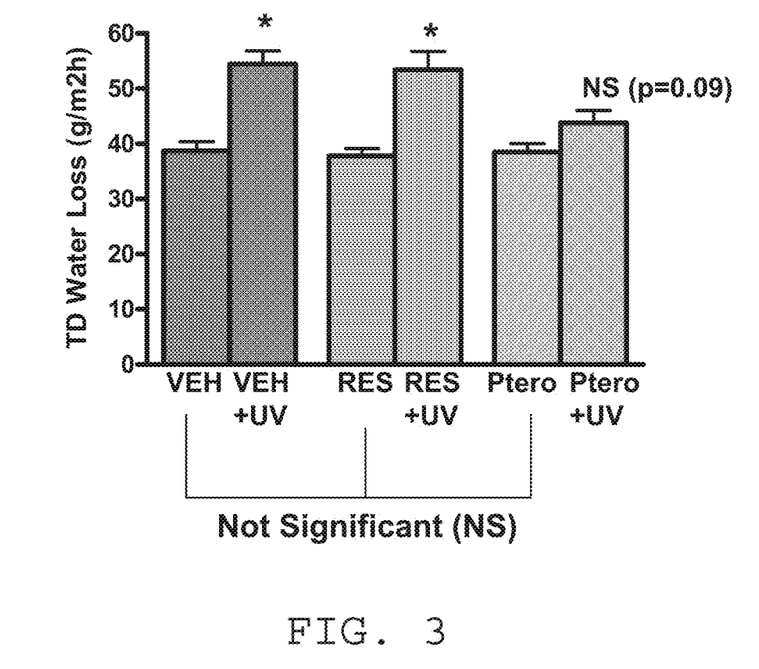
FIG. 3 depicts the manner in which pterostilbene prevents UV-mediated loss of skin barrier function in SKH-1 mice after exposure to UV-B radiation as described above for FIG. 2. TEWL measurements are expressed in g/m$^2$·h (and labeled 'TD Water Loss'). VEH=vehicle, RES=resveratrol, and PTERO=pterostilbene. * is p<0.01 and NS is not significant.

In certain embodiments, pterostilbene exhibits chemoprotective characteristics by preventing UV induced loss of barrier function in mouse skin (FIGS. 2 and 3). It has been shown herein that pterostilbene prevents TEWL after UV exposure (FIG. 3). Interestingly, pterostilbene was more effective than resveratrol in all cases (FIGS. 2 and 3). In fact, only pterostilbene prevented UV-mediated loss of barrier function. Resveratrol was ineffective. Thus, it is believed that pterostilbene will be effective in the prevention of numerous UV-mediated damages including cellular proliferative disorders of human skin.

Pterostilbene received GRAS (generally recognized as safe) certification in May 2011 and has been a commercially available nutraceutical marketed as a dietary supplement in pill form ever since. Clinically, pterostilbene went "first in humans" in December 2010 at the University of Mississippi with cholesterol, blood pressure and oxidative stress as endpoints (clinicaltrials.gov identifier number NCT01267227). In this study, a reduction in overall blood pressure was observed along with no toxicity reported in patients taking 125 mg of pterostilbene orally twice a day (Riche, D. M., et al., "Analysis of safety from a human clinical trial with pterostilbene," *J. Toxicol*. (2013) 2013: 463595). Thus, pterostilbene is an ideal agent to prevent UV-mediated skin damage based on its human safety profile.

(Example A) Pterostilbene is more bioavailable than resveratrol in vitro.

Figure 1:
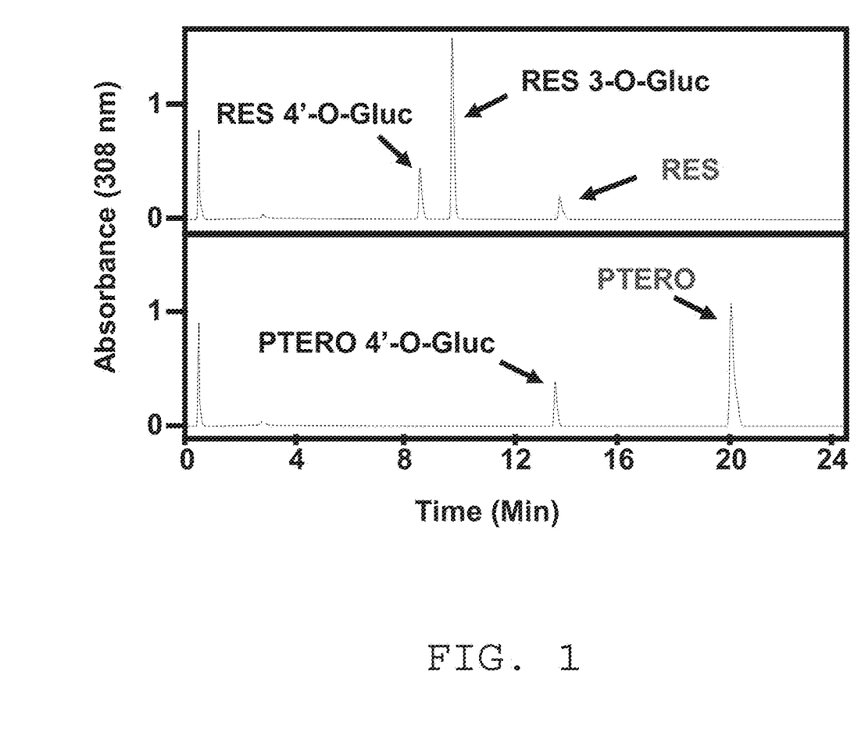
FIG. 1 depicts metabolism of resveratrol and pterostilbene. Human liver microsomes metabolize resveratrol much faster than pterostilbene. In vitro glucuronidation assays are shown examining the ability of 100 µg of human liver microsomes to glucuronidate either 500 µM resveratrol (RES; upper panel) or 500 µM pterostilbene (PTERO; lower panel) in 2 hours. HPLC chromatographs are presented depicting either parent compound or indicated glucuronide metabolite. Glucuronide metabolite peaks were confirmed by subsequent treatment with β-glucuronidase (data not shown). Detection of peaks by UV/VIS detector at 308 nm.

Using pooled human liver microsomes (n=20) it was demonstrated for the first time that resveratrol is metabolized much faster than pterostilbene (See, FIG. 1). Specifically, in vitro glucuronidation assays were performed as previously described in one co-inventor's work (Dellinger, R. W., et al., "Glucuronidation of PhIP and N—OH-PhIP by UDP-glucuronosyltransferase 1A10," *Carcinogenesis* (2007) 28: 2412-8; Dellinger, R. W., et al., "Importance of UDP-glucuronosyltransferase 1A10 (UGT1A10) in the detoxification of polycyclic aromatic hydrocarbons: decreased glucuronidative activity of the UGT1A10139Lys isoform," *Drug Metab. Dispos*. (2006) 34: 943-9; Chen, G., Dellinger, R. W., et al., "Glucuronidation of tobacco-specific nitrosamines by UGT2B10," *Drug Metab. Dispos*. (2008) 36: 824-30) using 100 μg of pooled human liver microsomes to assay the relative rates of glucuronidation of resveratrol vs. pterostilbene. After 2 hours, resveratrol was almost completely converted to its glucuronides (FIG. 1; upper panel), while pterostilbene is only 20% metabolized (FIG. 1; lower panel) indicating that pterostilbene will have a significantly higher half-life in humans. Consistent with previous reports, the 3-OH position of resveratrol is the preferred site of glucuronidation, while that position is methylated (and thus cannot be glucuronidated) in pterostilbene (Aumont, V., et al., "Regioselective and stereospecific glucuronidation of trans- and cis-resveratrol in human," *Arch. Biochem. Biophys*. (2001) 393: 281-9).

Furthermore, increased bioavailability of pterostilbene has been demonstrated conclusively in rats, where pterostilbene showed 5-fold increased bioavailability in comparison to resveratrol (Kapetanovic, I. M., et al., "Pharmacokinetics, oral bioavailability, and metabolic profile of resveratrol and its dimethylether analog, pterostilbene, in rats," *Cancer Chemother. Pharmacol*. (2011) 68: 593-601).

The overall rationale for studying nonmelanoma skin cancer (NMSC), particularly squamous cell carcinoma (SCC) and its precursors (including DNA damage of skin cells), emanates from its high and increasing frequency as the population ages, relative ease of accessibility of human tissue, increasing morbidity and mortality in immunocompromised individuals; SCC of the skin also serves as a potential model for understanding the biology of many other epithelial cancers.

Thus the methods described above may be further understood in connection with the following additional examples.

Reagents. Resveratrol and pterostilbene were obtained from ChromaDex Inc. (Irvine, Calif.). Six week old female SKH-1 hairless mice were purchased from Charles River Labs (Willington, Mass.). Anti-CPD (clone TDM2) and anti-64 PP (clone 64M-2) antibodies purchased from CosmoBio USA (Carlsbad, Calif.).

UV-B exposure. Mice were exposed to a single dose of 180mJ/cm$^2$ UVB radiation delivered via broadband UVB lamps (TL 40W/12 RS; Philips) emitting 290-350 nm light with a peak emission at 312 nm. The irradiance was measured using a thermopile sensor (818P-001-12; Newport Inc., Irvine, Calif.) and power meter (842-PE; Newport Inc.).

ELISAS. DNA was isolated from snap frozen whole back skin using Qiagen QIAamp Blood mini kit (cat#51104) per manufacturer's instructions. ELISAs were performed on purified DNA with anti-CPD (clone TDM2) and anti-64 PP (clone 64M-2) antibodies using manufacturer's protocol and read using a DTX 800 Multimode Detector plate reader (Beckman Coulter) using standard settings from colorimetric detection. Four technical replicates were used and DNA-free wells were used as negative control.

TEWL measurement. For transepidermal water loss (TEWL) a closed measurement chamber device (VapoMeter, Delfin Technologies Ltd, Kuopio, Finland) measuring flux density (gram/m$^2$·h) was used applying the sensor with even and constant pressure to dorsal skin by a single operator per manufacturer's instructions.

Statistics. All statistical analyses were performed using CRAN R, version 3.0.0, an open-source program of The R Foundation for Statistical Computing. Linear mixed-effect models were fit for each endpoint with a random effect for the mouse and fixed effects for UV exposure, treatment group, and their interaction.

EXAMPLE 1

Pterostilbene treatment preventing harmful UV-B-mediated damage including Transepidermal Water Loss (TEWL) in the skin of SKH-1 mice.

Hairless SKH-1 mice were used to evaluate the effectiveness of pterostilbene at preventing UV-mediated damage in skin. The SKH-1 model is ideally suited for this purpose and is commonly used in preclinical studies and yielded valuable results. Previously, resveratrol has been demonstrated to prevent aberrant alterations in mouse skin (Reagan-Shaw, S., et al., 2004). To ascertain if pterostilbene could also prevent those molecular alterations, we replicated these experiments. Specifically, 15 adult female SKH-1 (hairless) mice were subjected to UV-B radiation (180 mJ/cm$^2$) 30 minutes after topical application of vehicle (acetone), resveratrol or pterostilbene (5 mice each group), on their dorsal skin. For all topical treatments 200 µl total volume was applied to the back skin of the mouse. For acetone group, 200 µl of acetone was applied. For the resveratrol and pterostilbene groups the appropriate stilbene was applied at a concentration of 10 µmol/0.2 ml acetone/mouse. These mice were treated every 2 days for 7 total treatments. As a control, 15 mice were treated with topical vehicle, resveratrol or pterostilbene but not exposed to UV-B (5 mice each group). 24 hrs after last treatment, mice were euthanized, skin bi-fold measurements taken and back skins collected. As shown in FIGS. 2 and 3, pterostilbene prevented UV-B-induced damage in mouse skin. Visually, pterostilbene clearly prevented redness (sunburn) on back skin as compared to vehicle+UV-B treated (FIG. 2; compare far right panel to far left panel). In fact, no redness was observed on any of the 5 mice in the pterostilbene+UV-B group. Further, while resveratrol was able to limit the amount of redness observed on the back, it did not prevent it like pterostilbene did (FIG. 2; compare far right panel to middle panel). This prevention of visual skin damage by pterostilbene correlated nicely with the prevention of loss of barrier function. Specifically, pterostilbene prevented UV-mediated TEWL as compared to vehicle+UV-B (FIG. 3). In comparison, resveratrol did not prevent TEWL (FIG. 3). Therefore pterostilbene prevented UV-induced loss of barrier function of the skin of SKH-1 mice. This is the first demonstration that pterostilbene was effective in the prevention of loss of barrier function in skin. Interestingly, pterostilbene was more effective than resveratrol in all cases.

EXAMPLE 2

In another embodiment, efficacy of oral pterostilbene in the prevention of UV-mediated SCC in SKH-1 mice can be demonstrated.

The above data clearly demonstrated that pterostilbene can prevent UV-mediated damage (including loss of barrier function) in the skin of SHK-1 mice. To determine if pterostilbene is efficacious in the prevention of SCC, the ability of pterostilbene to prevent UV-induced SCC in SKH-1 mice will be examined. SKH-1 mice will be used here as this model is particularly susceptible to UV-induced skin carcinogenesis (Dickinson S. E., et al., "p38 MAP kinase plays a functional role in UVB-Induced mouse skin carcinogenesis," *Mol. Carcinog.* (2011) 50(6): 469-478). Eighty female SKH-1 mice (6 weeks old) will be obtained through the University of California—Irvine (UCI) mouse core facility and allowed to acclimate for 15 days prior to beginning experiments. Mice will be housed there in accordance with standards set by the Institutional Animal Care and Use Committee (IACUC) at UC Irvine. Mice will be allowed food and water ad libitum. Forty female SKH-1 mice (6 weeks old) will be randomly divided into two groups. The first group of animals will receive pterostilbene (in a 0.5% methylcellulose solution) by oral gavage three times a week (200 mg/Kg body weight). The second group of animals will receive oral vehicle (0.5% methylcellulose solution) by oral gavage and will serve as age-matched, untreated controls. Two weeks after first treatment mice will be exposed to UV irradiation using a solar simulator as previously described (Papazoglou, E., et al., "Noninvasive assessment of UV-induced skin damage: comparison of optical measurements to histology and MMP expression," *Photochem. Photobiol.* (2010) 86: 138-45). UV treatments will be performed weekly for 25-weeks. The initial dose will be 0.9 kJ/m$^2$ UV-B and increased each week by 25% until the final dose is reached at 2.75 kJ/m$^2$ UV-B, which will be continued for the duration of the experiment. Skin tumors will be counted and measured using digital caliper weekly. At the conclusion of the 25 weeks mice test groups will be sacrificed. Back skins and tumors will be excised for further analysis. The time of tumor appearance, number and size of tumors as well as lifetime survival will be recorded for individual mice to evaluate the effectiveness of treatments compared to corresponding control group.

Evaluation of biomarkers in normal skin and SCC of SKH-1 mice. To examine the effect of pterostilbene on AA signaling in our model examples, changes in expression levels from normal skin and tumors from the control mice will be assessed and compared to normal skin and tumors from pterostilbene treated mice. Concentrations of 12-HETE and PGE$_2$ will be assessed in normal skin and tumors from the control mice and compared to normal skin and tumors from pterostilbene treated mice after the 25 week treatment period using liquid chromatography coupled to a triple quad mass spectrometer (LC/MS/MS) as previous described (Maskrey, B. H., et al. "Analysis of eicosanoids and related lipid mediators using mass spectrometry," *Biochem. Soc. Trans.* (2008) 36: 1055-9). The concentrations of pterostilbene in mouse skin will also be assessed by LC/MS/MS as previously described (Kapetanovic, I. M., et al., 2011) to ensure effective delivery of pterostilbene to the skin. Protein levels of COX-2, 12-LOX, UGT and 15-PGDH will be measured semi-quantitatively by Western blot. DNA damage response proteins (e.g., p53 and H2AX) and angiogenesis (e.g., VEGF) will also be assessed in normal and tumor tissue. Detection of DNA damage (long term) will also be evaluated (both CPD and 64 pp).

The mouse models as described herein indicate that pterostilbene will be efficacious in the prevention or treatment of UV-mediated skin cancer. In addition, the data generated here supports the use of pterostilbene (e.g., applied topically) to treat, inhibit or prevent UV-mediated loss of barrier function in skin in mammals, including human subjects.

More specifically, since we have demonstrated that pterostilbene is effective in preventing loss of barrier function in skin as measured by preventing TEWL, pterostilbene is expected be useful in treating or preventing (and potentially repairing) loss of barrier function in burn injuries of mammalian (e.g., human) skin. Management of water loss is a critical component in the care of burn victims and novel, effective treatments are urgently needed.

In other embodiments, pterostilbene may be used in a cosmetic formulation to treat, inhibit or prevent UV-mediated damage in human skin. For example, a pterostilbene-containing composition can be used to treat, inhibit or prevent UV-induced skin wrinkles, stretch marks, and the like.

The skin cells as described are susceptible to UV light-induced damage, DNA damage, hyperplasia, and carcinogenesis. Also, normal aging in combination with UV-induced damage may contribute to formation of wrinkles, age spots, loss of skin elasticity, and other signs of aging including superficial wrinkles, a coarse deep wrinkle, enlarged pores, photodamage, scaliness, flakiness, dryness, sagging in skin, puffiness in skin around eye, puffiness in skin around jowl, loss of skin firmness, loss of skin tightness, loss of skin recoil from deformation, discoloration, blotching, sallowness, hyperpigmentation, keratosis, hyperkeratinization, elastosis or collagen breakdown, and cellulite, or combinations thereof Therefore, in an embodiment, methods of treatment comprising administration of pterostilbene may be used as follows: to improve certain UV-induced signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of skin recoil from deformation, discoloration, blotching, sallowness, hyperpigmentation, keratosis, hyperkeratinization, elastosis or collagen breakdown, and cellulite, or combinations thereof.

Additionally, the data herein provide support for the ability of pterostilbene to treat, inhibit or prevent a wide array of human cellular proliferative disorders including, but not limited to, benign hyperplasia (such as Psoriasis), keloid formation, AK formation, NMSC, as well as skin cancer (e.g., BCC, or SCC).

Therefore, in other embodiments of the method, pterostilbene can be administered by any route of administration described herein (e.g., topical) to treat, inhibit or prevent proliferative disorders including, but not limited to, benign hyperplasia (such as Psoriasis), keloid formation, AK formation, NMSC, as well as skin cancer (e.g., BCC, or SCC) in mammals, including humans.

When pterostilbene is used in a chemopreventive method, susceptible skin is treated prior to any visible condition affecting that skin (or, in some embodiments, any other evidence of loss of barrier function) in a particular individual. When pterostilbene is used to inhibit any of the conditions described above, pterostilbene may be applied to skin that exhibits evidence of one or more of these conditions or skin that exhibits no such evidence. When pterostilbene is used to treat any of the conditions described above, pterostilbene may be applied to skin that exhibits evidence of one or more of these conditions. Treatment of all skin can be achieved by systemic administration.

Useful therapeutic dosages of pterostilbene can range, but are not limited to, from about 1 mg to about 1000 mg in a human individual. Another suitable dose range is from about 5 mg to about 500 mg. Another suitable dose range is from about 20 mg to about 250 mg. Pterostilbene may be formulated as a pharmaceutical or nutraceutical composition, including a pharmaceutically or nutraceutically acceptable carrier, respectively. In one embodiment of a pharmaceutical composition containing pterostilbene, a suitable level of pterostilbene may range from about 0.1% by weight to about 10% by weight, based on the total weight of the composition.

The cosmetic or cosmeceutical compositions of the present invention may be administered in combination with a nutraceutically acceptable carrier. The active ingredients in such formulations may comprise from 1% by weight to 99% by weight, or alternatively, 0.1% by weight to 99.9% by weight. Alternatively, the active ingredients can range from about 5% by weight to about 75% by weight, or from about 10% by weight to about 75% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

In certain embodiments, the methods described herein reduce loss of barrier function in skin as indicated by decreasing transepidermal water loss (TEWL). In therapeutic methods, this reduction can be determined by measuring TEWL before and after initiating treatment. TEWL (e.g, of human subjects) can be measured by any suitable method, including that described herein.

The pharmaceutical (e.g., topical) compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

In accordance with certain embodiments, the topical pharmaceutical compositions disclosed herein can be provided in the form of an ointment, cream, lotion, gel or other transdermal delivery systems as described in L. V. Allen, Jr., et al., *Ansel's Pharmaceutical Dosage Forms and Drug Delivery Systems*, 9$^{th}$ Ed., pp. 272-293 (Philadelphia, Pa.: Lippincott Williams & Wilkins, 2011) which is incorporated herein by reference.

Ointments, as used herein, refer to semi-solid preparations including an ointment base having one or more active ingredients incorporated or fused (i.e., melted together with other components of the formulation and cooled with constant stirring to form a congealed preparation) therein. The ointment base may be in the form of: an oleaginous or hydrocarbon base (e.g., petrolatum or a petrolatum/wax combination); an absorption base which permits the incorporation of aqueous solution resulting in the formation of a water-in-oil emulsion (e.g., hydrophilic petrolatum) or which is a water-in-oil emulsion that permits the incorporation of additional quantities of aqueous solutions (e.g., lanolin); a water-removable base which are oil-in-water emulsions that may be diluted with water or aqueous solutions (e.g., hydrophilic ointment, USP); or a water-soluble base that do not contain oleaginous components (e.g., polyethylene glycol (PEG) formulations which combine PEGs having an average molecular below 600 with a PEG having an average molecular weight above 1,000); and the like.

Creams, as used herein, refer to semisolid preparations containing one or more active or medicinal agent dissolved or dispersed in either a water-in-oil emulsion or an oil-in-water emulsion or in another type of water-washable base. Generally, creams are differentiated from ointments by the ease with which they are applied/spread onto a surface such as the skin and the ease with which they are removed from a treated surface.

Lotions, as used herein, refer to suspensions of solid materials in an aqueous vehicle. Generally, lotions have a non-greasy character and increased spreadability over large areas of the skin than ointments, creams, and gels.

Gels, as used herein, refer to semisolid systems including a dispersion of small and/or large molecules in an aqueous liquid vehicle which is rendered jellylike by the addition of a gelling agent. Suitable gelling agents include, but are not limited to, synthetic macromolecules (e.g., carbomer polymers), cellulose derivatives (e.g., carboxymethylcellulose and/or hydroxypropyl methylcellulose), and natural gums (e.g., tragacanth gum, carrageenan, and the like). Gel preparations may be in the form of a single-phase gel in which the active or medicinal ingredients are uniformly dispersed throughout the liquid vehicle without visible boundaries or a two-phase gel wherein flocculants or small distinct particles of the active or medicinal ingredient are dispersed within the liquid vehicle.

Transdermal preparations may be formed from an ointment, cream, or gel that has been combined with a penetration enhancer and are designed to deliver an active or medicinal ingredient systemically. Penetration enhancers include, for example, dimethyl sulfoxide, ethanol, propylene glycol, glycerin, PEG, urea, dimethyl acetamide, sodium lauryl sulfate, poloxamers, Spans, Tweens, lecithin, and/or terpenes amongst others.

Other suitable semi-solid forms for use as cosmetic and/or topical pharmaceutical compositions include pastes (preparations containing a larger proportion of solid material rendering them stiffer than ointments) and glycerogelatins (plastic masses containing gelatin, glycerin, water, and an active or medicinal ingredient).

In other embodiments the topical and/or cosmetic compositions can be prepared in accordance with dosage forms as described in *Sample Preparation of Pharmaceutical Dosage Forms*, B. Nickerson, Ed. (New York: Springer, 2011) herein incorporated by reference.

Useful daily topical dosages of pterostilbene can range, but are not limited to, from about 1 mg to about 1000 mg in a human individual. Another suitable daily topical dose range is from about 5 mg to about 500 mg. Another suitable daily topical dose range is from about 20 mg to about 250 mg. Pterostilbene can be provided in daily topical dosages of from about 10 mg to about 250 mg, in a human patient, for example. Another suitable topical dosage range is from about 50 mg to about 150 mg daily. Another suitable topical dosage range is from about 50 mg to about 100 mg daily. A particularly suitable dosage is about 100 mg administered daily.

For oral administration, pterostilbene may be combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

In some embodiments, compositions useful in the methods described herein can include, in addition to pterostilbene, another active agent useful for treating, inhibiting or preventing the unwanted effects of UV, such as loss of barrier function in skin. For example, pterostilbene can be administered in a composition also containing any type of sunscreen, e.g., in topical and/or cosmetic compositions.

Routes of Administration

The compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of pterostilbene in the body of the patient in a controlled formulation, with systemic or local release of the drug to occur at a later time. For example, the drug may be localized in a depot for controlled release to the circulation, or for release to a local site of tumor growth.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about twelve weeks. The treatment schedule may be repeated as required.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for treating, inhibiting or preventing loss of barrier function in skin due to a burn injury, as indicated by transepidermal water loss (TEWL), the method comprising administering to an individual in need of such treatment an effective amount of the compound pterostilbene.

2. The method of claim 1, wherein the individual is a human.

3. The method of claim 2, wherein the pterostilbene compound is provided in a composition comprising a pharmaceutically or nutraceutically acceptable carrier.

4. The method of claim 3, wherein the effective amount of pterostilbene for a total dose is in a range of about 0.1% by weight to about 10% by weight based on the total weight of the composition.

5. The method of claim 4, wherein the effective amount of pterostilbene for a total daily dose is in a range of about 1 mg to about 1000 mg.

6. The method of claim 1, wherein the route of administration of the compound is selected from the group consisting of oral, topical, intradermal, transdermal, and subcutaneous.

7. The method of claim 1, wherein the route of administration is topical.

8. The method of claim 7, wherein the individual is a human.

9. The method of claim 8, wherein the pterostilbene compound is provided in a composition comprising a pharmaceutically acceptable carrier.

10. The method of claim 9, wherein the effective amount of pterostilbene for a total dose is in a range of about 0.1% by weight to about 10% by weight based on the total weight of the composition.

11. The method of claim 10, wherein the effective amount of pterostilbene for a total daily dose is in a range of about 1 mg to about 1000 mg.

12. The method of claim 1, wherein the method comprises measuring TEWL in the individual before and after administration of pterostilbene.

13. The method of claim 12, wherein the loss of barrier function indicated by TEWL is decreased, relative to the loss of barrier function expected for untreated skin.

* * * * *